United States Patent [19]

Milionis et al.

[11] Patent Number: 5,707,637
[45] Date of Patent: Jan. 13, 1998

[54] GRANULATED SOIL INSECTICIDAL-NEMATICIDAL COMPOSITIONS WITH REDUCED MAMMALIAN DERMAL TOXICITY

[75] Inventors: Jerry Peter Milionis, Somerset; James Arthur Behm, Hamilton Township, both of N.J.

[73] Assignee: American Cyanamid Company, Parsippany, N.J.

[21] Appl. No.: 479,501

[22] Filed: Jun. 7, 1995

Related U.S. Application Data

[63] Continuation-in-part of Ser. No. 302,944, Sep. 9, 1994, abandoned, which is a continuation of Ser. No. 624,892, Dec. 14, 1990, abandoned.

[51] Int. Cl.$^6$ .............................................. A01N 25/12
[52] U.S. Cl. ........................ 424/406; 424/413; 514/126
[58] Field of Search .................................. 424/405, 406, 424/408, 409, 413, 418, 485, 499; 514/126, 109

[56] References Cited

U.S. PATENT DOCUMENTS

| | | | |
|---|---|---|---|
| 4,485,103 | 11/1984 | Pasarela | 424/202 |
| 4,822,401 | 4/1989 | Tymonko | 71/87 |
| 4,891,223 | 1/1990 | Ambegaonkar | 424/408 |
| 4,923,506 | 5/1990 | Huber et al. | 71/121 |
| 5,143,539 | 9/1992 | Lovell | 71/92 |
| 5,290,753 | 3/1994 | Newhouse et al. | 504/214 |

FOREIGN PATENT DOCUMENTS

| | | |
|---|---|---|
| 2188651 | 10/1987 | United Kingdom. |
| 2214080 | 8/1989 | United Kingdom. |

*Primary Examiner*—Neil S. Levy
*Attorney, Agent, or Firm*—Gregory M. Hill

[57] ABSTRACT

There are provided new granulated soil insecticidal-nematicidal compositions with concomitant reduced mammalian dermal toxicities, comprising an inert granular, biodegradable, sorptive carrier of renewable resource material and an insecticidally and nematicidally effective amount of O,O-diethyl S-([(1,1-dimethylethyl)thio]methyl) phosphorodithioate or O,O-di-ethyl S-(ethylthiomethyl) phosphorodithioate.

7 Claims, No Drawings

GRANULATED SOIL INSECTICIDAL-NEMATICIDAL COMPOSITIONS WITH REDUCED MAMMALIAN DERMAL TOXICITY

This is a continuation-in-part of application Ser. No. 08/302,944, filed Sep. 9, 1994, now abandoned, which was a continuation of application Ser. No. 07/624,892, filed Dec. 14, 1990, now abandoned.

BACKGROUND OF THE INVENTION

For the past four decades farmers have employed soil insecticides and nematicides for the protection of their crops and control of soil borne pests in the locus thereof. Many of these insecticides and nematicides have $LD_{50}$'s at or below 50 mg/kg of animal body weight and are extremely toxic to mammals, including humans, when introduced into the circulatory systems thereof whether by dermal absorption, inhalation or ingestion. As such, it has been long recognized that extreme care must be taken when handling these toxic materials, as for example during the manufacture, packaging, transportation, distribution or the application thereof to the soil in the locus of the crops sought to be protected.

Two examples of soil insecticides that were developed nearly forty years ago and are still in as great demand today as they were in earlier years, are terbufos and phorate. These compounds are disclosed in the E. O. Hook et al U.S. Pat. Nos. 2,586,655 and 2,596,076 issued Feb. 19, 1952 and May 6, 1952; respectively.

Technical grade terbufos is reported in the Eight Edition of the Pesticide manual published by The British Crop Protection Council, to have an acute percutaneous $LD_{50}$ on rabbits of 1.0 mg/kg of animal body weight. Phorate is reported to have an acute percutaneous $LD_{50}$ on rats of 2.5–6.2 mg/kg of animal body weight.

Thus it is not surprising to find that during these past four decades the agricultural industry has sponsored an extensive research effort to find methods of reducing the oral and dermal toxicities of these extremely toxic insecticide-nematicides.

It wasn't until 1976 that A. D. Lindsay found that montmorillonite, a naturally occurring clay, is unique as a carrier for terbufos, i.e. O,O-diethyl S-([(1,1-dimethylethyl) thio]methyl)phosphorodithioate. He found that, in contrast to other conventional naturally occurring solid carriers, terbufos formulations prepared with montmorillonite are distinguished by decreased mammalian dermal toxicity. He also found that the temperature at which the montmorillonite is calcined is instrumental in imparting reduced dermal toxicities to the formulated product. This finding was reported by Lindsay in U.S. Pat. No. 4,059,700, issued Nov. 22, 1977, where it was shown that an $LD_{50}$ of 28.3 mg/kg of animal body weight is obtained with formulations prepared with montmorillonite calcined at 500°–700° C. and an $LD_{50}$ of 49.2 mg/kg of animal body weight is obtained with formulations prepared with montmorillonite calcined at 1,200°–1,300° C.

By 1982 N. R. Pasarela had determined that terbufos formulations having reduced mammalian dermal toxicity could also be prepared with 2% to 10% by weight of terbufos on corn cob grits by admixing therewith tall oil or vegetable oil in amounts ranging from about one half to about twice the weight of the terbufos present in the formulation. These formulations are disclosed in the Pasarela U.S. Pat. No. 4,313,940 issued Feb. 2, 1982. While the $LD_{50}$'s for said formulations are reported by the patentee as ranging from 149 to 260 mg/kg of animal body weight, such formulations are not entirely satisfactory since they are subject to some leakage problems in packaging, some stability problems (especially in warm climates) in storage and some problems in achieving uniform distribution of the product in the field due to agglomeration of particles.

Pasarela also described in U.S. Pat. No. 4,343,790 issued Aug. 10, 1982 and U.S. Pat. No. 4,485,103 issued Nov. 27, 1984, controlled release acrylic polymer coated granular pesticidal compositions with reduced dermal toxicity. The $LD_{50}$'s mentioned by Pasarela for these terbufos and phorate formulations are between about 40 mg/kg of animal body weight <200 mg/kg of animal body weight depending on the compound used and the concentration thereof in the formulation. These compositions are effective for control of soil borne insects and nematodes, however, said formulations tend to agglomerate during manufacture and thus are not entirely satisfactory for commercial use or large scale production.

It has also been found that when terbufos or phorate formulations are prepared on pumice or other abrasive carriers the applicators used for distribution of the formulated product are subject to severe wear and rapid erosion. Such erosion is costly and is a very significant problem especially in under developed and economically stressed countries.

In addition to the above-said difficulties encountered in the preparation of terbufos and phorate formulations having reduced dermal toxicity, it is now evident that the high grade minerals from naturally occurring deposits which have been previously employed as carriers for insecticides and nematicides are being depleted. Thus, the quality of the carriers available today is beginning to deteriorate and with such deterioration formulators are encountering problems in (1) maintaining pesticide levels in the formulated products, (2) retaining effectiveness of the products in the field and (3) maintaining the $LD_{50}$ levels once established for the formulated products.

It is therefore an object of the present invention to provide a new granulated pesticidal formulation composition having reduced mammalian dermal toxicity and comprising a solid inert granular, biodegradable, sorptive carrier obtained from a renewable resource and an insecticidally and nematicidally effective amount of O,O-diethyl S-([(1,1-dimethylethyl) thio]methyl)phosphorodithioate or O,O-diethyl S-(ethylthiomethyl)phosphorodithioate.

It is also an object of this invention to provide a particulated pesticide composition with concomitant reduced mammalian dermal toxicity, comprising; an inert granular carrier prepared from a cellulosic complex and having a uniform quality, particle size, shape, bulk density, absorption capacity and pH, and having absorbed therein an insecticidally-nematicidally, effective amount of terbufos or phorate. The cellulosic carriers used in the formulation of this invention are also essentially non-dusting and non-abrasive, but readily decompose in or on the soil in the presence of soil and moisture.

SUMMARY OF THE INVENTION

This invention relates to new granulated insecticidal-nematicidal compositions with reduced mammalian dermal toxicities, comprising; an inert granular, biodegradable, sorptive carrier of renewable resource material and an insecticidally and nematicidally effective amount of O,O-diethyl S-([(1,1-dimethylethyl)thio]methyl)

phosphorodithioate, (Terbufos) or O,O-diethyl S-(ethylthiomethyl)phosphorodithioate, (Phorate).

The renewable resource material is a cellulosic material preferably obtained as deinked paper, recycled or otherwise, or as waste material from paper manufacture such as sulfate, sulfate pulp or primary paper sludge. Other cellulosic materials that may be employed as the renewable resource material from which the sorptive granular carriers can be prepared for use in the compositions of this invention are wood fiber from trees and primary and secondary wood pulp or sludge.

Granular carriers that are especially useful in the preparation of the reduced dermal terbufos and phorate compositions of this invention generally have a bulk density of from 20 lbs/cft to 45 lbs/cft and preferably from 35 to 45 lbs/cft. They have a pH value between pH 6.0 and pH 8.0, contain from about 2.0% to 5.0% moisture, have a particle size in which at least about 90% by weight of the granules are −8, +48 mesh and preferably −8, +20 mesh, based upon U.S. Standard sieve sizes. They are comprised of about 37% to 60% by weight of fiber and contain about 63% to 40% by weight of fillers normally used in the manufacture of paper such as kaolin, barium sulfate, titanium dioxide and the like.

The granules that are used in the preparation of the compositions of this invention are distinguished from other granules heretofore employed as carriers for terbufos or phorate by reason of the fact that the above-said granules provide finished, free-flowing, non-abrasive granular compositions having significantly reduced mammalian dermal toxicities and provide slow release of the pesticide contained therein. The granules themselves can be prepared by the methods of manufacture described by H. E. Lowe et al in their UK patent GB 2188651B, application No. 8705107.4 filed Mar. 5, 1987. However, it should be noted that the patentees describe the preparation of such a broad class of granular compositions by their processes that many of the granular compositions prepared by the patentees are not entirely satisfactory for use in the preparation of the compositions of the present invention.

Only those granular compositions having the physical and chemical characteristics described above appear to provide the significantly improved mammalian dermal toxicities and controlled release rates of terbufos or phorate so vehemently sought after during the past four decades of research in the field of crop protection products.

In accordance with this invention, compositions containing from about 2.0% to 20% by weight of terbufos or phorate can be prepared by spraying a fluidized or tumbling bed of dry particulated cellulosic material with about 2.0% to 20.0% by weight of technical grade terbufos or phorate. The particle size of the cellulosic granules is generally at least about 90% by weight of −8 mesh +48 mesh particle size and comprises about 75% to 98% by weight of the finished terbufos or phorate cellulosic particulate product. In practice, controlled particle size ranges of 8/20, 10/14, 12/20, 12/24 or 24/48 mesh material are frequently used.

Spraying of the cellulosic particles is continued for about 10 to 30 minutes, after which the sprayed granules are tumbled or blended for an additional 10 to 60 minutes and preferably 20 to 60 minutes to allow the terbufos or phorate to be uniformly distributed throughout the particulate mass and well absorbed into each granule.

Where desired from about 2.0% to 7.0% by weight of vegetable oil or mineral oil may be applied as a liquid spray to the terbufos or phorate impregnated granules. However, unlike conventional terbufos or phorate granules prepared with montmorillonite, Mexican ROB (aluminum silicate), European Diaperl S-1 or the like, where the $LD_{50}$ of the pesticide granules have heretofore, been further improved by the addition of small amount of oil, with the compositions of the present invention addition of a small amount of vegetable or mineral oil is tolerable but generally tends to increase the dermal toxicity of the terbufos or phorate granules rather than reduce the dermal toxicity thereof.

A biocide may also be applied to the above-said granules to inhibit bacterial proliferation and the thus prepared granules may be dried using any convenient means, such as a fluid bed drier, belt dryer or the like.

In addition to the above-said procedures for preparing terbufos and phorate cellulosic granular compositions with markedly reduced mammalian dermal toxicity, it is also found that further improvement in the mammalian dermal toxicity can be obtained by coating or partially coating the terbufos or phorate granules, with about 1.0% to 10.0% by weight of a natural or synthetic resin or polymer such as shellac, lacquer, or an acrylic polymer, polyvinyl acetate (PVA) or a polyvinyl chloride (PVC) resin or polyvinyl chloride/vinyl ester copolymer or homopolymer having a weight average molecular weight of about 200,000 to 400,000 and an inherent viscosity, as determined by ASTMD 1243, of about 1.00 to 1.32. For example, the PVC coating composition is prepared by admixing said PVC resin with about 5.0% to 15.0%, by weight, of a plasticizing agent such as butyl benzyl phthalate, diisononyl phthalate, dibutyl phthalate, di-2-ethyl-hexyl phthalate, tricresyl phosphate and trioctyl phosphate; about 0.3% to 2.0%, by weight, of a heat stabilizing agent for the resin, such as an organotin stabilizer, organo barium stabilizer, zinc/calcium stearate, epoxidized soybean oil, dibasic lead phosphite or the like; and about 0.5% to 2.0%, by weight, of a surface active agent, such as a nonionic surfactant.

Nonionic surfactants useful in these PVC coating compositions include nonylphenoxy polyethoxyethanol, octylphenoxy polyethoxyethanol, alkylarylpolyether alcohol, alkyl polyether alcohol, mixtures thereof, or the like.

Polymers used in in the PVC coating compositions were marketed by B.F. Goodrich as Geon® 138.

Other plasticizers useful in the preparation of the above-said PVC coating compositions are epoxidized soybean oil, organic trimellitates, such as trioctyl mellitate or organic citrates such as acetyl tributylcitrate, or mixtures thereof.

Other stabilizing agents effective for stabilizing the PVC resins include stearates, such as alkaline earth metal stearates, epoxidized soybean oil, secondary octyl tins and phosphites and organo barium and cadmium complexes, or mixtures thereof.

Preferred PVC coated compositions of the present invention comprise about 2.0% to 20.0% by weight of terbufos or phorate; about 70.0% to 93.0%, by weight of a biodegradable, cellulosic granular material having a pH value between pH 6 and pH 8 and a particle size which is about 90% by weight −8 +48 mesh and coated with about 5.0% to 10.0%, by weight, of a polyvinyl chloride dispersion resin homopolymer/copolymer coating composition having a weight average molecular weight of about 260,000 to 340,000 and an inherent viscosity ASTMD 1243 of about 1.13 to 1.26 and containing about 5.0% to 15.0%, by weight, of a plasticizing agent selected from butyl benzyl phthalate and diisononyl phthalate; about 0.3% to 2.0%, by weight, of calcium/zinc stearate, a heat stabilizing agent for the resin; about 0.5% to 2.0% of the nonionic surfactant, nonylphenoxy polyethoxyethanol.

The PVC or PVC/vinyl ester copolymer or homopolymer composition employed for coating or partially coating the terbufos or phorate cellulosic granular compositions may be prepared by mixing together about 12.5% to 50.0% by weight of the PVC resin or PVC/vinyl ester copolymer or homopolymer with about 0.3% to 5.0% by weight of a heat stabilizing agent; about 5.0% to 37.5% by weight of a plasticizing agent; and about 0.58% to 5% by weight of a surface active agent. This composition can then be sprayed onto the tumbling bed of particulate cellulosic, biodegradable, sorptive carrier containing from about 2.0% to 20.0% by weight of terbufos or phorate. When spraying is complete, the particulate composition is introduced into a dryer or drum furnace where it is heated to a temperature between about 120° C. to 160° C. in order to cure the PVC resin coating on the granules.

Advantageously, the granulated formulations of this invention are highly effective for controlling symphylids, white grubs, seed corn beetles, billbugs, thrips, corn flea beetles, nematodes, wireworms, rootmaggots, cutworms, greenbugs, corn leaf aphids, Diabrotica spp., *Tetanops myopaeformis*, *Delia brassicae*, millipedes, onion maggots, and the like and may be applied to the soil in several ways. They may be applied to the soil surface as a broadcast application, a band beside the rows of planted crops, or a ring around individual plants such as in the case of banana trees. The compositions may also be applied in furrow when planting crops such as corn or in admixture with crop seeds such as canola, i.e. oil seed rape.

A surprising advantage obtained when utilizing the formulations of this invention is the slow release of the terbufos or phorate which has been absorbed into the cellulosic granules. These cellulosic granular formulations do not permit rapid release or a burst of terbufos or phorate into the soil when said granular formulation is applied. Rather, these formulations provide a metered release of toxicant into the soil. This is especially important when the above-said pesticides are being employed for crop protection against insects and nematodes and said crops are being treated for weed control with an acetohydroxyacid synthase (AHAS) inhibiting herbicide such as a sulfonylurea herbicide. Among the AHAS inhibiting herbicides, which have been reported to induce crop injury when used in conjunction with previously available terbufos compositions are primisulfuron and nicosulfuron.

Advantageously, the present invention provides a method for protecting crops, especially corn, from attack by insects and nematodes while inhibiting the growth of undesirable plant species in the presence of said crops by applying to soil in the locus of said crops, at or about the time of planting, an insecticidally-nematicidally effective amount of a cellulosic, granular composition at least 90% of which is −8, +48 mesh granules having a bulk density of from 20 lbs/cft to 45 lbs/cft and a pH value between pH6 and pH8 and absorbed therein from 2% to 20% by weight of terbufos and thereafter applying to the locus of the said terbufos treated crops approximately 2 to 4 weeks after planting and after said crops have emerged, a herbicidally effective amount of an AHAS inhibiting herbicide, said method reducing or eliminating crop injury due to interaction between terbufos and the AHAS inhibiting herbicide.

The method of the present invention is especially useful for reducing or eliminating crop injury due to interaction between terbufos and an AHAS inhibiting herbicide when at least 90% of the cellulosic, granular composition is −8, +20 mesh granules having a bulk density of from 35 lbs/cft to 45 lbs/cft and a pH value between pH6 and pH8 and absorbed therein from 5% to 15% by weight terbufos.

The cellulosic, granular compositions of this invention may be applied in furrow with the crop seeds at the time of planting, as a band beside the planted crop rows at or near the time of planting or broadcast over the planted crop rows at or near the time of planting. The compositions of the present invention are particularly useful for reducing or eliminating corn injury due to the interaction between terbufos and a sulfonylurea herbicide such as primisulfuron and nicosulfuron.

Advantageously, the present invention provides a method for reducing or eliminating crop injury due to the interaction between terbufos and an AHAS inhibiting herbicide without requiring the incorporation of a herbicide insensitive AHAS enzyme into the crop. In one of the preferred embodiments of the present invention, the crops are not altered by the incorporation of a resistance gene encoding a herbicide insensitive AHAS enzyme.

In practice, it is found that the application of a sufficient quantity of the cellulosic granular composition of the invention, to provide about 0.25 kg/ha to 8.0 kg/ha, preferably about 0.25 kg/ha to 4.0 kg/ha of the insecticide-nematicide, to the soil in which plants are planted or growing, will protect said plants from attack by insects and nematodes. Moreover, it is found that such treatment will provide extended protection for the plants against insect and nematode attack.

In order to facilitate a further understanding of the invention, the following examples are presented primarily for the purpose of illustrating certain more specific details thereof. The invention is not to be deemed limited thereby except as defined in the claims.

EXAMPLE 1

5% Terbufos Cellulosic Granular Insecticide-nematicide Composition Having Reduced Mammalian Dermal Toxicity A horizontal rotary blender is charged with 750 gm of inert 12/20 mesh granular biodegradable, cellulosic sorptive particles having a pH value of 7.15 and a bulk density of 38.5 lbs/cft. Said cellulosic granules are about 39.0% by weight of cellulose fiber, 58% by weight of kaolin and about 4% by weight of titanium dioxide and/or barium sulfate from the manufacture of paper. The particle size distribution of the cellulosic granules is as follows:

| U.S. Sieve Size | % By Weight |
| --- | --- |
| #8 | 0 |
| #10 | 0 |
| #12 | 0.97 |
| #16 | 79.04 |
| #20 | 17.39 |
| #30 | 1.74 |
| pan | 0.84 |

The blender is started and the tumbling mass of particulate material sprayed with 51 gm of technical grade terbufos (86.0% purity). Spraying is continued for twelve minutes and the sprayed mass blended for an additional ten minutes to assure even distribution of the terbufos throughout the particulate mass and excellent absorption into each particle. The composition thus prepared is then screened to assure a 12/20 mesh product having a minimal amount of fines and essentially no oversize. The bulk density of the finished product is 46.3 lbs/cft. The product is then stored in glass containers until the formulation is assayed for stability, attrition, mammalian toxicity and/or biologically evaluated.

To determine stability of the terbufos in the above-said particulate composition, said composition is placed in a glass storage vessel and stored at 45° C. for two months. The initial terbufos assay indicates the presence of 5.48% terbufos in the composition. Two months after storage at 45° C. the product is again assayed and found to contain 5.43% terbufos.

Resistance to attrition of the terbufos composition is found to be very high from the day of preparation and, surprisingly, improves during storage as can be seen below.

| | Resistance to Attrition (%) | | |
|---|---|---|---|
| Initial | 1 Month | 2 Months | 3 Months |
| 98.0% | 98.8% | 99.2% | 99.6% |

The mammalian dermal toxicity of the thus prepared composition is determined on male rabbits and the Rabbit Dermal $LD_{50}$ is found to be 453 [326–627] mg/kg.

EXAMPLE 2

5% Terbufos Cellulosic Granular Insecticide-Nematicide Composition Having Reduced Mammalian Dermal Toxicity The procedure of Example 1 is repeated excepting that 10/14 mesh inert, biodegradable, cellulosic sorptive particles are substituted for the 12/20 mesh particles used in said example 1. The cellulosic granules are approximately 40% by weight cellulose fiber, 57% by weight of kaolin and 3% by weight of titanium dioxide and/or barium sulfate from the manufacture of paper. The particle size distribution of the cellulosic granules based on U.S. Sieve Size is as follows:

| U.S. Sieve Size | % By Weight |
|---|---|
| #8 | 0 |
| #8–10 | 4.97 |
| #10–14 | 67.44 |
| #14–16 | 18.16 |
| #16–50 | 9.43 |
| –30 | 0 |

The bulk density of these granules is 35.7 lbs/cft and they have a pH value of 7.7.

The blender is charged with 750 gm of the above-said cellulosic particles and sprayed with 53.43 gm of technical grade terbufos (88.0% purity) for twelve minutes. After spraying of the terbufos is complete, the sprayed particles are sprayed with 0.75 gm of Red Dye Sudan IV and then blended for an additional ten minute period.

The bulk density of the finished product is 39.2 lbs/cft and has a Rabbit Dermal of $LD_{50}$ of 343 [244–482] mg/kg.

The finished product comprises on a parts by weight basis 5.85% terbufos, 0.01% Red Dye Sudan IV and 94.14% cellulosic granules 10/14 mesh.

EXAMPLE 3

5% Terbufos Plus 5% Soybean Oil Cellulosic Granular Insecticide-Nematicide Composition Having Reduced Mammalian Dermal Toxicity The procedure of Example 2 is repeated excepting that the 750 gm of 10/14 mesh cellulosic particles are sprayed with 57.04 gm of technical grade terbufos (88% purity), then with 50 gm of soybean oil and thereafter 0.75 gm of Red Dye Sudan IV. The sprayed particles are blended for an additional ten minutes and then placed in a clear glass bottle.

Determination of the dermal toxicity of the thus prepared composition indicates a Rabbit Dermal toxicity of 207 [167–258] mg/kg on male rabbits.

On a parts by weight basis the finished product is 5.85% terbufos, 0.01% Red Dye Sudan IV, 5.85% Soybean Oil and cellulosic granules 10/14 mesh 88.29%.

EXAMPLE 4

10% Terbufos Cellulosic Granular Insecticide-Nematicide Composition Having Reduced Mammalian Dermal Toxicity A horizontal rotary blender is charged with 750 gm of inert 8/20 mesh granular, biodegradable, cellulosic sorptive particles having a pH value of 7.15 and a bulk density of 38.5 lbs/cft. Said cellulosic granules are about 38% by weight of cellulose fiber, 58% by weight of kaolin and about 4% by weight of titanium dioxide and/or barium sulfate used in the manufacture of paper. The particle size distribution of the cellulosic granules is as follows:

| U.S. Sieve Size | % By Weight |
|---|---|
| #8 | 0.2 |
| #10 | 0.4 |
| #14 | 81.7 |
| #16 | 14.4 |
| #25 | 3.3 |
| pan | 0 |

The blender is started and the tumbling mass of particulate material sprayed with 100.0 gm of technical grade terbufos (86.0% purity). Spraying is continued for twelve minutes and the sprayed mass blended for an additional ten minutes to assure even distribution of the terbufos throughout the particulate mass and excellent absorption into each particle. The composition, thus prepared, is then screened to assure an 8/20 mesh product having a very minimal amount of fines and essentially no oversize. The product is stored in a glass bottle until analyzed and found to contain 10.2% terbufos. The Rabbit Dermal $LD_{50}$ for this product is 171 [122–214] mg/kg. It has a finished bulk density of 46.3 lbs/cft.

The finished product is 10.20% by weight terbufos and 89.80% by weight 8/20 mesh cellulosic granules.

EXAMPLE 5

10% Terbufos Cellulosic Granular Insecticide-Nematicide Composition Having Reduced Mammalian Dermal Toxicity The procedure of Example 4 is repeated excepting that 12/20 mesh cellulosic granular material is substituted for the 8/20 mesh material used in said Example 4. The finished product has a bulk density of 46.3 lbs/cft and a Rabbit Dermal $LD_{50}$ of 226 [163–314]-mg/kg. Addition of 2.0% by weight of linseed oil to the thus prepared product increases the mammalian dermal toxicity of the oil containing product giving it a Rabbit Dermal $LD_{50}$ 171 [122–214] mg/kg.

EXAMPLE 6

15% Terbufos Cellulosic Granular Insecticide-Nematicide Composition Having Reduced Mammalian Dermal Toxicity A horizontal rotary blender is charged with 85 parts by weight of 8/20 mesh granular, biodegradable, cellulosic sorptive particles having a bulk density of 38.5 lbs/cft and a pH value of 7.15. The blender is rotated and sprayed with 17.04 parts by weight of technical grade terbufos (88% purity). Spraying of the terbufos is conducted for twelve minutes and the sprayed mass is permitted to blend for fifteen minutes thereafter. The thus prepared product contains 15% by weight of terbufos and has a Rabbit Dermal $LD_{50}$ of 143 [73–276] mg/kg.

The above-described procedure is repeated excepting that 12/20 mesh cellulosic granules are substituted for the 9/20 mesh granules used in the above-said composition. The product contains 15% by weight of terbufos and has a Rabbit Dermal $LD_{50}$ of 135 [82–221] mg/kg.

EXAMPLE 7

15% Phorate Cellulosic Granular Insecticide Composition Having Reduced Mammalian Dermal Toxicity Following the procedure of Example 1, but substituting technical grade phorate (86% purity) for terbufos and substituting 24/48 mesh granular, biodegradable, cellulosic sorptive particles having a bulk density of 41.6 lbs/cft and a pH value of 7.5 for the 12/20 mesh cellulosic particles of Example 1, yields the above mentioned 15% phorate composition.

This is accomplished by charging a blender with 85 parts by weight of 24/48 mesh cellulosic granules as described above, starting said blender and spraying the tumbling or moving particles with 17.4 Parts by weight of technical grade phorate (86% purity). After spraying is completed the particles are blended for an additional fifteen to twenty minutes to assure even distribution of phorate throughout the mass and excellent absorbency into each particle. The resulting 15% phorate composition is stored in a glass bottle until evaluated for dermal toxicity. The composition is found to have a Rabbit Dermal $LD_{50}$ of 260[161–420] mg/kg.

EXAMPLE 8

20% Phorate Cellulosic Granular Insecticide Composition Having Reduced Mammalian Dermal Toxicity The procedure of Example 7 is repeated excepting that 80 parts by weight of 24/48 cellulosic granules are sprayed with 23.26 parts by weight of technical grade phorate (86% purity). The resulting composition has a Rabbit Dermal $LD_{50}$ of 80[51–127] mg/kg.

EXAMPLE 9

5% Terbufos composition on Eastern Europe Diaperl S-1 and Mexican ROB (aluminum silicate) carriers with reduced mammalian dermal toxicity Following the procedure of Example 1, but substituting 94.86 parts by weight of 24/48 mesh Eastern Europe Diaperl S-1 carrier for the cellulosic granules of example 1 and spraying said carrier with 5.85 parts by weight of technical grade terbufos (88% purity) yields a 5% terbufos Diaperl S-1 composition. The composition is stored in a glass bottle until evaluated for mammalian toxicity. This 5% terbufos composition has a Rabbit Dermal $LD_{50}$ of 120[99–154] mg/kg.

The above procedure is repeated using 24/48 mesh Mexican ROB (aluminum silicate) as the carrier for the 5% terbufos composition. The Rabbit Dermal $LD_{50}$ for this terbufos composition is 49 mg/kg.

EXAMPLE 10

10% Terbufos compositions prepared on Costa Rican pumice and South African montmorillonite The above-said compositions are prepared by charging a blender with 88.64 parts by weight by 10/20 mesh Costa Rican pumice granules. The blender is started and the tumbling mass of particles sprayed for 10 minutes with 11.36 parts by weight of technical grade terbufos (88% purity). The sprayed particulate mass is blended for an additional 20 minutes after spraying is complete in order to provide even distribution of the terbufos throughout the mass. The thus prepared 10% terbufos composition is stored in a glass bottle until it is evaluated for mammalian toxicity. The Rabbit Dermal $LD_{50}$ for this composition is 52 mg/kg.

The procedure is repeated excepting that 24/48 mesh South African montmorillonite is substituted for the 10/20 Costa Rican pumice. The prepared product is then placed in a glass bottle until evaluated for mammalian toxicity. The Rabbit Dermal $LD_{50}$ for this 10% terbufos composition is 136 [123–149] mg/kg.

EXAMPLE 11

15% Terbufos Compositions Prepared on United States Montmorillonite

A blender is charged with 82.56 parts by weight of 24/48 mesh montmorillonite obtained from a U.S. deposit. The blender is set into motion and the tumbling mass of particles sprayed with 17.44 parts by weight of technical grade terbufos (86.0% purity). Spraying is continued over a 10 minute period and the sprayed mass permitted to blend for 20 minutes after spraying is ceased. The thus prepared 15% terbufos composition is stored in a glass bottle until evaluated for mammalian toxicity. The Rabbit Dermal $LD_{50}$ for this composition is 10.2 mg/kg.

EXAMPLE 12

15% Phorate Compositions on Sand and Montmorillonite Carrier

A blender is charged with 85.00 parts by weight of 24/48 mesh sand and then set into motion. The tumbling sand particles are then sprayed with 17.44 parts by weight of phorate (86.0% purity). Spraying is conducted over a 10 minute period and the sprayed particle blended for an additional 15 minutes after spraying is completed. The resulting particles are stored in a glass bottle until evaluated for mammalian toxicity. The thus prepared composition has a Rabbit Dermal $LD_{50}$ of 28 mg/kg.

The above procedure is repeated excepting that montmorillonite from a U.S. source is substituted for the sand. The montmorillonite 15% phorate is stored in a glass bottle until mammalian toxicity is determined. The Rabbit Dermal $LD_{50}$ for this composition is 129 mg/kg.

EXAMPLE 13

20% Phorate Composition Prepared on Attapulgite and Montmorillonite Granules

A blender is charged with 76.7 parts by weight 24/48 mesh attapulgite clay granules. The blender is set into motion and the tumbling bed of granules sprayed over a 12 minute period with 23.3 parts by weight of technical grade phorate (86% purity). When spraying is completed the granules are blended for an additional 20 minutes to assure uniform distribution of the phorate throughout the particulate mass. The resulting composition is then stored in a glass bottle until mammalian dermal toxicity of the composition is determined. The thus prepared 20% by weight phorate composition has a Rabbit Dermal toxicity $LD_{50}$ of 37 mg/kg.

The procedure is repeated excepting that 24/48 mesh montmorillonite granules are substituted for 24/48 attapulgite granules. The Rabbit Dermal $LD_{50}$ for this 20% by weight phorate composition is 64 mg/kg.

EXAMPLE 14

Determination of Rabbit Dermal toxicities for all compositions described in Examples 1–13 above In these tests, albino male rabbits of the New Zealand white strain and approximately 12 to 14 weeks of age are weighted and placed in individual cages equipped with an automatic watering device. The rabbits are fed ad libitum a non-medicated Purina Rabbit chow. Each animal is identified using a metal ear tag.

The test site is prepared on each animal by clipping the trunk free of hair with electric clippers and a number 40 blade approximately 24 hours prior to testing. The test material, as received, is spread on a plastic wrap, moistened with tap water, the rabbit is placed ventral surface down on the wrap with the test material and the plastic wrap secured to the animal with adhesive tape. The area is then covered with a filter cloth wrapping to protect the plastic from damage. The area of application encompasses approximately 10% of the body surface area. The test material is held occluded under the impervious plastic wrap in continuous 24 hour contact with the shaved skin. At the end of the 24 hour exposure period the wraps are removed and any remaining test material removed by wiping the test site the cloth wrap.

The treated animals are examined daily for toxic signs such as ataxia, salivation and prostration and death.

The toxic signs (if any) and death are recorded for each animal and the results of the observations recorded. The $LD_{50}$ calculations are then undertaken using the Weil Method.

Comparative Rabbit Dermal toxicity data, mg/kg for the compositions prepared in examples 1–13 above are reported in Tables I and II below, where it can be seen that terbufos and phorate compositions prepared on the new cellulosic granules have significantly improved $LD_{50}$'s compared to compositions prepared on carriers obtained for non-renewable natural resources.

TABLE I

Rabbit Dermal toxicity data: $LD_{50}$'s for 5% to 15% by weight of terbufos on a variety of granular carriers

| Compound % by weight terbufos | Granular Cellulosic carrier U.S. mesh size | Dermal $LD_{50}$ mg/kg | Granular Mineral carrier U.S. mesh size | Dermal $LD_{50}$ mg/kg |
|---|---|---|---|---|
| 5% | 12/20 | 453[326–627] | 24/48 Eastern European Diaperl S-1 | 120[99–154] |
| 5 | 10/14 | 343[244–482] | 24/48 Mexican ROB | 49 |
| 5% + 5% oil | 10/14 | 207[167–258] | | |
| 10% | 8/20 | 171[122–214] | 10/20 Costa Rican Pumice | 52 |
| 10% | 12/20 | 226[163–314] | 24/48 South African montmorillonite | 136[123–149] |
| 10% + 2% oil | 12/20 | 171[122–214] | | |
| 15% | 8/20 | 143[73–276] | 24/48 U.S. montmorillonite | 10.2 |
| 15% | 12/20 | 135[82–221] | | |

TABLE II

Rabbit Dermal toxicity data: $LD_{50}$'s for 15% to 20% by weight of phorate on a variety of granular carriers

| Compound % by weight terbufos | Granular Cellulosic carrier U.S. mesh size | Dermal $LD_{50}$ mg/kg | Granular Mineral carrier U.S. mesh size | Dermal $LD_{50}$ mg/kg |
|---|---|---|---|---|
| 15% | 24/48 | 260[161–420] | 24/48 sand | 28 |
| | | | 24/48 U.S. montmorillonite | 129 |
| 20% | 24/48 | 80[51–127] | 24/48 attapulgite | 37 |
| | | | 24/48 U.S. montmorillonite | 64 |

EXAMPLE 15

Preparation of Terbufos Cellulosic Granular Insecticide-Nematicide Composition Partially Coated with Shellac and Having a Reduced Mammalian Dermal Toxicity A 400.0 gm sample of the terbufos composition prepared as described in Example 5 above is introduced into a bench top tumbler and the tumbler set in motion. A 1.36 kg can of white shellac (30.7% solids) is then well stirred and a 50 gm sample of the shellac taken from the can and sprayed on the surface of the tumbling mass of 10% terbufos. Since the shellac adheres to the surfaces of the spraying equipment on 23.88 gms of shellac is actually applied to the particles. Spraying is completed in about 3 minutes, but, the sprayed granules are permitted to tumble for an additional 20 minutes and until the particles have a shiny appearance. To assist drying the treated granules are permitted to tumble and subjected to blowing with a stream of air. The finished granules are only partially coated and contain about 1.8% by weight of shellac.

EXAMPLE 16

Preparation of Terbufos Cellulosic Granular Insecticide-Nematicide Composition Partially Coated With an Acrylic polymer and having a reduced mammalian dermal toxicity The procedure of example 15 is repeated excepting that an acrylic polymer marketed by Rohm Pharmaceutical Co. as Eudragit-E is used as the coating material. In this preparation 400.0 gm of the 10% terbufos granules prepared as in Example 5 are placed in a bench top tumbler and the tumbler set in motion. This tumbling particles are then Sprayed with 12.5 gm of the acrylic polymer Eudragit-E dispersed in 100 mL of acetone. Spraying is carried out over a 70 minute period and then tumbled for an additional 30 minutes with air being blown into the tumbler for the purpose of drying the particles. As the acrylic polymer adheres to equipment only 33.3 gm of the polymer is actually applied to the particles surfaces. This yields particles having 1.04% by weight of acrylic polymer as a partial coating.

EXAMPLE 17

Biological Evaluation of Terbufos Cellulosic Granular Insecticide-Nematicide Composition Having Reduced Mammalian Dermal Toxicity In these tests, banana trees are treated with a semi-circular application of the terbufos applied to the soil on cellulosic or pumice granules. The root systems are examined at 30 day intervals following application. Results obtained are as follows:

A biological evaluation of terbufos cellulosic granular insecticide-nematicide for the control of banana nematodes (*Radopholus similis*) indicate the formulation is effective in reducing these nematodes similar to the pumice formulation. Nematode counts obtained following June 26 applications in bananas are as follows:

| Formula- | | Dosage | No. of Radodophulus similis/100 g roots | | |
|---|---|---|---|---|---|
| tion | Carrier | (gm ai/mat) | July | Aug. | Sept. |
| Terbufos 15% G | (cellulose) | 3.0 | 11,000 | 8,917 | 7,417 |
| Terbufos 10% | (pumice) | 3.0 | 7,000 | 7,167 | 13,000 |

At 3 months after treatment, the cellulosic formulation is maintaining the Radopholus populations numerically below the economic threshold level of 10,000/100 g roots for an extended period compared to the pumice formulation. The nematode control for both treatments is reflected in the plant response in percent functional roots.

| Formula- | | | Functional Roots (%) | | |
|---|---|---|---|---|---|
| tion | Carrier | (gm ai/mat) | July | Aug. | Sept. |
| Terbufos 15% G | (cellulose) | 3.0 | 87.3 | 85.6 | 80.4 |
| Terbufos 10% | (pumice) | 3.0 | 85.5 | 85.9 | 80.0 |

The results indicate the cellulosic formulation of terbufos is equal to the pumice formulation which is recognized as highly effective in the control of nematodes present in banana plantations.

EXAMPLE 18

Evaluation of the Interaction Between Two Pesticides

Soil (Indiana Tippycanoe silt-loam) is placed in 6-inch round pots and moistened. A furrow is made in each pot and the appropriate granular terbufos composition is applied into the furrow at a rate equivalent to 1.1 kg/ha of active ingredient. Two corn seeds are then placed into each furrow and the furrows are back-filled. The pots are placed on greenhouse benches, watered and cared for in accordance with conventional greenhouse procedures.

After 10 days, a commercial formulation of primisulfuron which contains 75% of active ingredient (BEACON® 75DF, manufactured by Ciba-Geigy Co), is diluted with water to provide the equivalent of 0.055 kg/ha of active ingredient to the foliage when applied through a spray nozzle operating at 40 psi for a predetermined time. The herbicide spray solution contains 0.25% of the spray adjuvant X-77, a non-ionic wetting agent containing alkylaryl polyoxyethylene, glycols, free fatty acids and isopropanol, manufactured by Valent USA Corp.

After spraying, pots are placed on greenhouse benches, watered and cared for in accordance with conventional greenhouse procedures. Twenty-six days after spraying, the tests are terminated and each pot is examined and rated by measuring the height of the foliage. The test results are averaged and expressed as a percent growth reduction compared to an untreated check, using the following formula:

% Growth Reduction =

$$100 - \left[ \frac{\text{Height of Treated Plants}}{\text{Height of Untreated Plants}} \times 100 \right]$$

The results are summarized in Table III in which composition A is a 15% terbufos cellulosic granular composition (13/20 mesh cellulosic granules, prepared according to the procedure of Example 6) and B is the commercial 15% terbufos granular composition (COUNTER® 15G, manufactured by American Cyanamid Company).

TABLE III

| Treatment | Rate (kg/ha) | % Growth Reduction |
|---|---|---|
| Untreated check | 0.00 | 0 |
| Primisulfuron | 0.055 | 0* |
| A + Primisulfuron | 1.1 + 0.055 | 8 |
| B + Primisulfuron | 1.1 + 0.055 | 54 |

Shoot height of the untreated check is 73.5 cm
*Growth is 2% greater than the untreated check As can be seen from the data in Table III, the interaction between the acetohydroxyacid synthase-inhibiting herbicide, primisulfuron, and the organophosphate insecticide-nematicide, terbufos, is significantly reduced for the terbufos cellulosic granular composition of the invention (treatment A) compared to the terbufos montmorillonite granular composition of the art (treatment B).

EXAMPLE 19

Preparation of a Terbufos Cellulosic Granular Composition Coated With a Polyvinyl Alcohol Resin A blender is charged with inert 13/20 mesh granular, biodegradable, cellulosic sorptive particles having a pH value of about 7.0 to 8.0 and a bulk density of about 40 lbs/cft (BIODAC® 12/20, manufactured by Edward Lowe Industries, Inc.). The granules are about 50% by weight of cellulosic fiber, about 31% by weight of kaolin, about 17% by weight of calcium carbonate and less than 1% by weight of titanium dioxide. The blender is started and the tumbling mass of particulate material sprayed with technical grade terbufos (85% purity). Spraying is continued for 20 minutes and the sprayed mass is blended for an additional 20–25 minutes to assure even distribution of the terbufos throughout the particulate mass and absorption into each particle.

To coat the granules, the terbufos granules prepared above are placed on a 24 inch. tablet coating pan, the pan is rotated at 20 rpm and the granules are sprayed with a polyvinyl alcohol coating solution containing polyvinyl alcohol resin (AIRVOL® 103, Air Products and Chemicals, Inc.), glycerin (SUPEROL®, Proctor and Gamble, Co.), a 1,2-benzisothiazolin-3-one solution (PROXEL® GXL, ICI Americas, Inc.) an antifoam agent (Antifoam 30® IND, Harcros Chemicals, Inc.) and water. The granules are dried during the coating procedure by maintaining the pan temperature at 110° F. and dried for an additional 5–10 minutes to give coated 15% terbufos cellulosic granules having the following composition:

| Ingredient | wt/wt % |
| --- | --- |
| Terbufos technical (85% active) | 17.650 |
| Granular, cellulosic particles | 79.350 |
| Polyvinyl alcohol resin | 2.635 |
| Glycerin | 0.316 |
| PROXEL ® GXL | 0.028 |
| Antifoam 30 ® IND | 0.021 |

EXAMPLE 20

Field Evaluation of the Interaction Between Terbufos and AHAS Inhibiting Herbicides Corn seeds are planted in fields containing sandy loam or loam soil and the appropriate granular terbufos composition is applied in furrow at the time of planting at a rate of 1.1 kg/ha of active ingredient. When the corn plants have grown to the 4 to 6 leaf stage, herbicidal compositions containing the AHAS inhibiting herbicide primisulfuron or nicosulfuron, 0.25% v/v ORTHO X-77 (a spray adjuvant manufactured by Valent USA Corp.) and water are sprayed onto the corn plants at a rate of 0.055 kg/ha for primisulfuron and 0.048 kg/ha for nicosulfuron. Fourteen days after herbicide application, the corn plants are visually evaluated for injury compared to an untreated check. The results are summarized in Table IV wherein composition A is the coated 15% terbufos cellulosic, granular composition prepared in Example 19 and B is the commercial 15% terbufos granular composition (COUNTER® 15G, manufactured by American Cyanamid Company).

TABLE IV

| Treatment | Rate (kg/ha) | % Injury |
| --- | --- | --- |
| Untreated Check | 0.0 | 0.0 |
| Primisulfuron | 0.055 | 1.3 |
| A + Primisulfuron | 1.1 + 0.055 | 7.1 |
| B + Primisulfuron | 1.1 + 0.055 | 12.8 |
| Nicosulfuron | 0.048 | 2.4 |
| A + Nicosulfuron | 1.1 + 0.048 | 7.2 |
| B + Nicosulfuron | 1.1 + 0.048 | 12.1 |

As can be seen from the data in Table IV, the interactions between the acetohydroxyacid synthase-inhibiting herbicides, primisulfuron and nicosulfuron, and the organophosphate insecticide-nematicide, terbufos, are significantly reduced for the terbufos cellulosic granular composition of the invention (treatment A) compared to the terbufos montmorillonite granular composition of the art (treatment B).

EXAMPLE 21

Field Evaluation of the Interaction Between in Furrow Terbufos Applications and AHAS Inhibiting Herbicides Corn seeds are planted in fields containing sandy loam or loam soil and the appropriate granular terbufos composition is applied in furrow at the time of planting at a rate of 1.32 kg/ha of active ingredient. When the corn plants have grown to the 4 to 6 leaf stage, herbicidal compositions containing the AHAS inhibiting herbicide primisulfuron or nicosulfuron, 0.05% v/v ORTHO x-77 (a spray adjuvant manufactured by Valent USA Corp.) and water are sprayed onto the corn plants at a rate of 0.040 kg/ha for primisulfuron and 0.035 kg/ha for nicosulfuron. Fourteen and twenty-one days after herbicide application, the corn plants are visually evaluated for injury compared to an untreated check. The results are summarized in Table V wherein composition A is a 15% terbufos cellulosic, granular composition (12/20 mesh cellulosic granules, prepared according to the procedure of Example 6), B is the coated 15% terbufos cellulosic, granular composition prepared in Example 19, and C is the commercial 15% terbufos granular composition (COUNTER® 15G, manufactured by American Cyanamid Company).

TABLE V

| | | % Injury | |
| --- | --- | --- | --- |
| Treatment | Rate (kg/ha) | 14 DAT[1] | 21 DAT |
| Untreated check | 0.0 | 0 | 0 |
| A + Primisulfuron | 1.32 + 0.040 | 38 | 38 |
| B + Primisulfuron | 1.32 + 0.040 | 57 | 52 |
| C + Primisulfuron | 1.32 + 0.040 | 88 | 83 |
| A + Nicosulfuron | 1.32 + 0.035 | 30 | 22 |
| B + Nicosulfuron | 1.32 + 0.035 | 43 | 32 |
| C + Nicosulfuron | 1.32 + 0.035 | 73 | 47 |

[1]DAT = days after herbicide application

As can be seen from the data in Table V, the interactions between the acetohydroxyacid synthase-inhibiting herbicides, primisulfuron and nicosulfuron, and the organophosphate insecticide-nematicide, terbufos, are significantly reduced for the terbufos cellulosic, granular compositions of this invention (treatments A and B) compared to the terbufos montmorillonite, granular composition of the art (treatment C).

EXAMPLE 22

Field Evaluation of the Interaction Between Banded Terbufos Applications and AHAS Inhibiting Herbicides Corn seeds are planted in fields containing sandy loam or loam soil and the appropriate cellulosic, granular terbufos composition of the invention is applied banded at the time of planting at a rate of 1.32 kg/ha of active ingredient. When the corn plants have grown to the 4 to 6 leaf stage, herbicidal compositions containing the AHAS inhibiting herbicide primisulfuron or nicosulfuron, 0.05% v/v ORTHO X-77 (a spray adjuvant manufactured by Valent USA Corp.) and water are sprayed Onto the corn plants at a rate of 0.040 kg/ha for primisulfuron and 0.035 kg/ha for nicosulfuron. Fourteen and twenty-one days after herbicide application, the corn plants are visually evaluated for injury compared to an untreated check. The results are summarized in Table VI wherein composition A is a 15% terbufos cellulosic, granular composition (12/20 mesh cellulosic granules, prepared according to the procedure of Example 6), and B is the coated 15% terbufos cellulosic, granular composition prepared in Example 19.

TABLE VI

| Treatment | Rate (kg/ha) | % Injury | |
| --- | --- | --- | --- |
| | | 14 DAT[1] | 21 DAT |
| Untreated check | 0.0 | 0 | 0 |
| A + Primisulfuron | 1.32 + 0.040 | 15 | 18 |
| B + Primisulfuron | 1.32 + 0.040 | 21 | 22 |
| A + Nicosulfuron | 1.32 + 0.035 | 10 | 5 |
| B + Nicosulfuron | 1.32 + 0.035 | 25 | 15 |

[1]DAT = days after herbicide application

We claim:

1. A method for protecting crops from attack by insects and nematodes while inhibiting the growth of undesirable plant species in the presence of said crops which comprises applying to soil in the locus of said crops, at or about the time of planting, an insecticidally-nematicidally effective amount of a cellulosic, granular composition at least 90% of which is −8, +48 mesh granules having a bulk density of from 20 lbs/cft to 45 lbs/cft and a pH value between pH6 and pH8 and absorbed therein from 2% to 20% by weight of terbufos and thereafter applying to the locus of the said terbufos treated crops approximately 2 to 4 weeks after planting and after said crops have emerged, a herbicidally effective amount of an acetohydroxyacid synthase (AHAS) inhibiting herbicide,. said method reducing or eliminating crop injury due to interaction between terbufos and the AHAS inhibiting herbicide.

2. The method according to claim 1 wherein at least 90% of the cellulosic, granular composition is −8, +20 mesh granules having a bulk density of from 35 lbs/cft to 45 lbs/cft and a pH value between pH6 and pH8 and absorbed therein from 5% to 15% by weight of terbufos.

3. The method according to claim 1 wherein the terbufos granules are applied at the time of planting to the soil surface as a band beside the planted crop rows and the herbicide is applied to the locus of the crops after they have emerged and are at the 2 to 6 leaf stage.

4. The method according to claim 1 wherein the AHAS inhibiting herbicide is a sulfonylurea herbicide.

5. The method according to claim 4 wherein the sulfonylurea herbicide is primisulfuron.

6. The method according to claim 4 wherein the sulfonylurea herbicide is nicosulfuron.

7. The method according to claim 8 wherein said crops are corn.

* * * * *